United States Patent
Bianchetti et al.

(10) Patent No.: US 6,857,873 B2
(45) Date of Patent: Feb. 22, 2005

(54) OPTICAL SYSTEM FOR A DENTAL HANDPIECE FOR POLYMERIZATION OF PHOTOSETTING COMPOUNDS OR RESINS

(75) Inventors: Fernando Bianchetti, Chiavari (IT); Domenico Vercellotti, Sestri Levante (IT)

(73) Assignee: Mectron S.r.l., Genova (IT)

( * ) Notice: Subject to any disclaimer, the term of this patent is extended or adjusted under 35 U.S.C. 154(b) by 221 days.

(21) Appl. No.: 10/253,945

(22) Filed: Sep. 23, 2002

(65) Prior Publication Data

US 2003/0096211 A1 May 22, 2003

(30) Foreign Application Priority Data

Nov. 22, 2001 (EP) .............................................. 01830722

(51) Int. Cl.⁷ ................................................. A61C 1/00
(52) U.S. Cl. ....................................................... 433/29
(58) Field of Search ........................... 433/29; 362/555, 362/558, 259, 337, 339, 119

(56) References Cited

U.S. PATENT DOCUMENTS 5,030,090 A * 7/1991 Maeda et al. ................. 433/29
6,159,005 A * 12/2000 Herold et al. ................. 433/29
6,419,483 B1 * 7/2002 Adam et al. ................... 433/29
6,611,110 B1 * 8/2003 Fregoso ....................... 315/224
2003/0036031 A1 * 2/2003 Lieb et al. .................... 433/29

FOREIGN PATENT DOCUMENTS

| EP | 0798788 A1 | 1/1997 |
| WO | WO 01/64129 A1 | 7/2001 |

* cited by examiner

*Primary Examiner*—Todd E. Manahan
(74) *Attorney, Agent, or Firm*—Sheridan Ross PC

(57) ABSTRACT

An optical system for the polymerization of photosetting compounds or resins is described. The optical system includes a LED mounted on a heat dissipater inside the body of a dental handpiece and an optical fibre or light guide mounted at the top of the handpiece to convey and emit at, its output end, the light emitted by the LED so as to direct it onto the area in which the photosetting compound or resin is to be polymerized. The system also includes an optical element or optical conveyor able to couple the LED with the optical fibre to convey the light beam emitted by the LED toward the input of the optical fibre, said optical element being of such a shape as to minimize dispersion of the light beam emitted by the LED thereby acting as a light beam concentrator.

1 Claim, 5 Drawing Sheets

—— Vertical angle
······ Horizontal angle

—— Vertical angle
······ Horizontal angle a0 1028.999
a1 943.249
a2 771.749
a3 600.249
a4 85.750 b0 823.1989
b1 754.5990
b2 617.3992
b3 342.9995
b4 68.5999

| | |
|---|---|
| c0 | 775.9528 |
| c1 | 500.0000 |
| c2 | 400.0000 |
| c3 | 250.0000 |
| c4 | 100.0000 |

# OPTICAL SYSTEM FOR A DENTAL HANDPIECE FOR POLYMERIZATION OF PHOTOSETTING COMPOUNDS OR RESINS

DESCRIPTION

The present invention relates to an optical system for a dental handpiece for the polymerization of photosetting compounds or resins.

The dental handpiece is an instrument employed by dental surgeons for the polymerization of photosetting compounds or resins utilised especially in dental prostheses.

Photosetting resins are applied in a semisolid state to patients' dental prostheses and are then hardened by a polymerization process. Such a polymerization process involves heating the resins for a certain length of time by means of a light source that emits blue light, i.e. having an emission spectrum with a wavelength centred around 470 nm.

Handpieces according to the prior art currently use halogen lamps as their light source. The light coming from the halogen lamps is filtered by dichroic filters, so that a blue light having a light spectrum with a wavelength between 430 and 510 nm is obtained. The light emerging from the dichroic filters is conveyed, through optic fibres, to the outlet of the dental handpiece, enabling the dentist to direct it onto the resin to be polymerized, applied to the patient's dental prosthesis.

The known dental hand-pieces using halogen lamps as polymerizing lamps have various drawbacks.

In order to achieve polymerization of the resin, the light emerging from the dental hand-piece must have an output power of approximately 500 mW. Since halogen lamps have a very low power efficiency (efficiency value $\eta=0.5-1\%$), this results in a high energy dissipation by the polymerizing lamps, which reaches values between 50 and 100 W. Consequently, excessive overheating of the handpiece occurs leading to problems in heat dissipation. In fact, to aid heat dissipation large-sized handpieces have to be used, sometimes provided with internal ventilation systems.

As a result, these handpieces are excessively bulky and heavy, at the expense of manoeuvrability.

Furthermore, with the output power that can be obtained from halogen lamps, rather long resin polymerization times are required; this can be very tiresome both for the patient undergoing the procedure and for the dental surgeon who has to perform it.

In an effort to reduce resin polymerization times, handpieces with different light sources have been put on the market. Handpieces are per se known that use as their light source gas-discharge lamps (plasma torches), which emit high-power white light that is filtered in order to obtain a light beam with an emission spectrum centred on blue. Also known are dental handpieces using laser as their light source, which directly transmit a light beam with an emission spectrum centred on blue.

With this type of dental handpiece it is possible to obtain a light beam having a power output approximately ten times greater than that obtained with halogen lamps, therefore shorter polymerization times are achieved. However, such dental handpieces, apart from being very expensive, have the problem of needing to dissipate a large amount of heat and inevitably they must provide a heat dissipating system or a cooling system, making them excessively bulky and heavy.

All known handpieces using halogen lamps, plasma torches or laser as their light source have an independent electrical supply system, dedicated solely to the electrical supply of said light sources. As a result the dental handpiece is bulky and lacks versatility because of the purpose-built circuitry provided for such light sources.

Patent application PCT/GB 98/02905 describes an optical radiation device suitable for polymerization, using as its light source an array of light emitting diodes (LED) of the type commonly available on the market, that is to say comprising a semi-conductor junction covered by a covering package of transparent material.

In order to increase the number of LEDs in the array, the covering package of each led is faceted so that the LEDs can be placed side by side to occupy the minimum space. This device has the drawback that a large number of LEDs is necessary to focus a sufficient light beam for polymerization. Thus to fit the largest possible number of LEDs into a small surface, such as that available inside a dental handpiece, it is necessary to facet the protective package of each LED, with a consequent waste of time and expense for additional processing. Despite this, the proposed LED arrays continue to be excessively bulky.

Patent application PCT WO 99/35995 describes a device for polymerization by means of radiation using as its light source arrays of LED dies mounted on a printed circuit board.

The dies are parallelepiped-shaped chips, not provided with any protective packaging. The dies consist of a semiconductor junction that emits light when polarized. In this solution, despite the fact that a die emitting light from six surfaces, only the light emission from the upper surface is exploited.

In fact, the dies are mounted on a planar printed circuit board on which the bump and metal tracks provided for the electrical connection inhibit propagation of the light flux coming from the side surfaces of the dies. Consequently, the energy available is about one-fifth of that provided by said die. As a result, the device according to patent application WO 99/35995 requires a very large number of dies (about 100) to reach a sufficient power to achieve polarization.

This leads to various drawbacks. In fact, there are manufacturing complications in housing such a high number of dies in a printed circuit board of limited dimensions. Furthermore, since the light efficiency of each die is not exploited to the full, there is a high formation of heat, due in part to the light energy of the dies that is not exploited. This leads to considerable drawbacks in the design of adequate heat dissipators such as to allow operation of the device.

The object of the present invention is to eliminate said drawbacks by providing an optical system for a dental handpiece for polymerization of photosetting compounds or resins that is of limited overall dimensions, is versatile, economical and simple to produce.

This object is achieved in accordance with the invention with the characteristics listed in appended claim 1.

Preferred embodiments of the invention will become apparent from the dependent claims.

The optical system for a dental handpiece for the polymerization of photosetting compounds or resins according to the invention comprises a light source mounted within the body of the handpiece and an optical fiber or wave guide mounted at the top of the handpiece and coupled to the light source in order to convey and emit the light coming from the light source so as to direct it onto the area in which the photosetting compound or resin is to be polymerized.

The peculiarity of the invention lies in the fact that the light sources comprises a single high-flux LED and the optical system comprises an optical element able to connect the LED with the optical fibre to convey the light beam coming from the LED to the input end of the optical fibre. The optical element is of such a shape as to minimize dispersion of the light beam emitted by the LED, so as to increase the light transmission efficiency of the optical system to have as the output from the optical fibre a light beam with sufficient luminous intensity to polymerize photosetting compounds.

The advantages of the invention are obvious in that it allows a single LED with a dedicated optic to be used, with a resulting saving in components, assembly and bulk.

Further characteristics of the invention will be made clearer by the detailed description that follows, referring to a purely exemplary and therefore non-limiting embodiment thereof, illustrated in the appended drawings, in which.

The optical system for a dental handpiece for polymerization of photosetting resins or compounds according to the invention will be described with reference to the figures.

Figure 1:
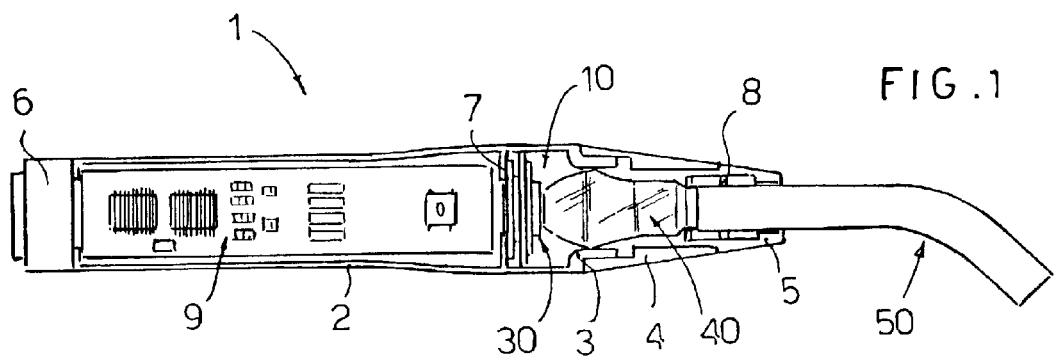
FIG. 1 is a diagrammatic part-sectional axial view of a handpiece with the optical system according to the invention.

FIG. 1 illustrates a dental handpiece designated, as a whole, by reference numeral 1. The handpiece 1 comprises a substantially hollow cylindrical body 2. At its front end, the body 2 has a threaded connector 3 provided with an external thread to couple with a first threaded nut 4, provided with an internal thread, having a substantially frusto-conical shape. The first nut 4 couples with a second nut 5, having an external thread, and forming the top of the handpiece 1.

An optical system according to the invention, designated as a whole by reference numeral 10, is mounted in the front end of the body 2 of the handpiece, inside the first nut 4 and inside the second nut 5.

Figure 2:
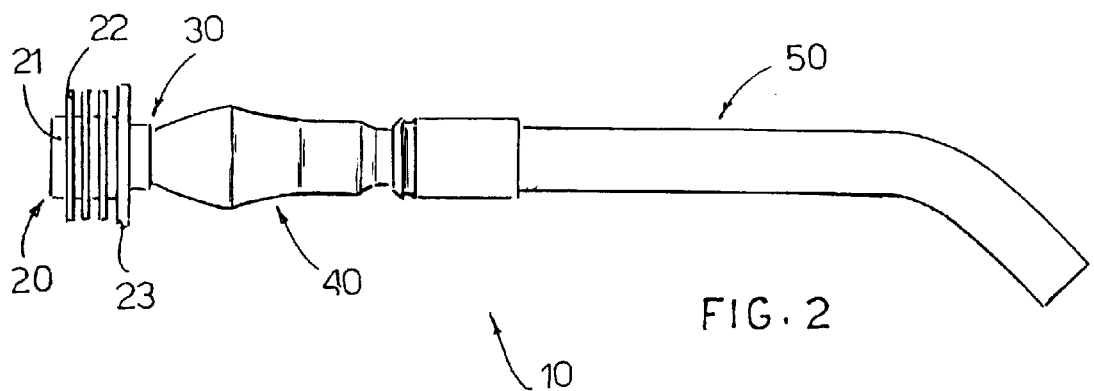
FIG. 2 is a side view of the optical system of FIG. 1, assembled.

As better shown in FIG. 2, the optical system 10 comprises a heat dissipator 20, a high-flux, high-efficiency LED 30 mounted on the heat dissipator 20, an optical element or optical conveyor 40 coupled to a LED 30 and an optical fibre 50 coupled to the optical element 40.

The optical element 40 is supported by the connector 3 and by the front part of the body of the handpiece and the optical fibre 50 is supported by a fixing element 8 disposed in the inner surface of the second nut 5. In this manner, the axis of the optical fibre 50 is perfectly aligned with the axis of symmetry of the optical element 40. Furthermore the fixing nut 5 allows easier removal and insertion of the optical fibre 50 which must often be dismantled to be subjected to high-temperature sterilization.

At the tail end of the body 2 of the handpiece is a cover 6 wherein is situated an electrical connector element having electrical contacts for the electrical supply and earthing of the internal circuitry of the handpiece. The connector can be connected to a complementary connector element to be able to take its power supply from the electrical mains or from a dentist's unit. The dentist's unit is provided with electrical transformers that take the power supply from the electrical mains and provide a supply voltage of 24V alternating current or of 32 V direct current. Handpieces can also be provided without a connector with autonomous supply systems such as batteries able to provide a suitable DC voltage for powering the LED 30.

The electrical contacts of the connector are connected to a printed circuit board 9 positioned inside the body 2 of the handpiece. Various electronic components, chips and integrated circuits which regulate operation of the handpiece 1 are mounted on the printed circuit board 9 and are not illustrated in detail being the subject of European patent application EP 1.090.608 in the name of the same applicant. The printed circuit board is connected to the contacts of the LED 30, through electric cables.

Returning to the optical system 10 which is the subject of the present invention, the heat dissipator 20 has a central body 21 from which a plurality of fins 22 protrude radially. The dissipator 20 is fixed to a flange 7 in the front part of the body 2 of the handpiece and has at its front a flange 23 for centring thereof inside the front part of the body of the handpiece.

A high-efficiency LED 30 is mounted on the front end of the dissipator 20. As better shown in FIG. 3, the LED 30 is mounted on a thin printed circuit board 31 which in turn is glued to a second flat dissipator 32 in the form of an aluminium plate. The second flat dissipator 32 is coupled to the first finned dissipator 20. In this manner, the thermal efficiency of the LED 30 is increased and at the same time overheating of the hand-piece I is decreased during operation of the LED 30.

The LED 30, by way of example, can be a high-output LED (High-Flux) commonly known commercially with the trademark LUXEON™ and produced by Lumileds Lighting. The LED 30 preferably emits light in the blue range (430–510 nm) and has an emission power of about 120 mW.

The optical element 40 is substantially cylindrical in shape and is made of methacrylate. The optical element 40 has axially, in its rear end, an outwardly open recessed seat 41 to receive the LED 30. The seat 41 has a truncated ellipsoidal side surface and ends at the front in a paraboloid-shaped wall 42 with its convexity facing inside the seat 41 and its axis coinciding with the axis of the optical element 40.

Figure 3:
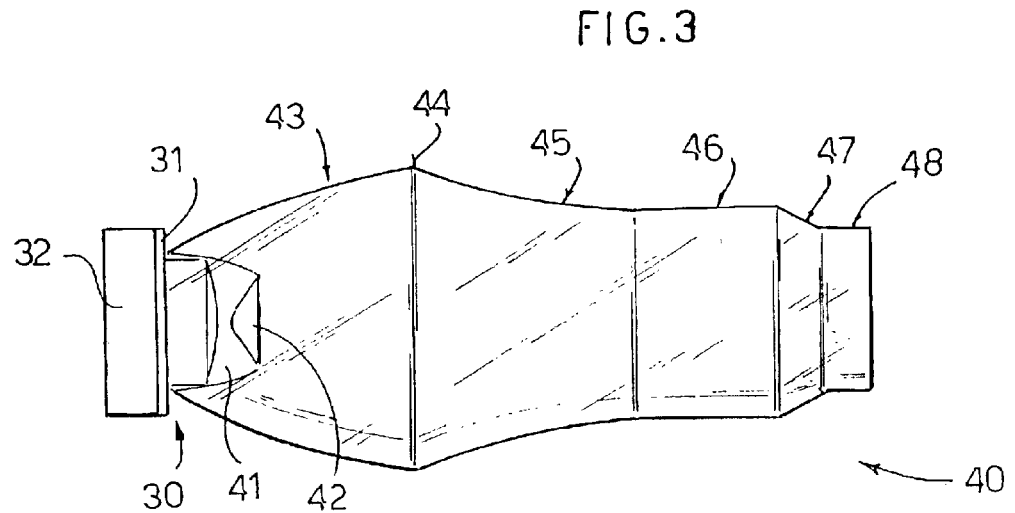
FIG. 3 is a side view of a LED and an optical element coupled together, both forming part of the optical system according to the invention.

With reference to FIG. 3, from left to right, that is to say form the rear part (input of the light beam) to the front part (output of the light beam), the optical element 40 has a side profile comprising a first, rear portion 43, with a substantially frusto-conical shape, with an increasing diameter, ending in a larger diameter part 44. The larger diameter part 44 continues with a second intermediate portion 45, with a substantially frusto-conical shape, with a decreasing diameter. The second intermediate portion 45 continues with a third intermediate portion 46, substantially cylindrical in shape, that continues with a tapered part 47 with a decreasing diameter, ending with a smaller diameter front end part 48 with a substantially cylindrical shape.

The front end part is cut with a plane at right angles to the axis of the optical element and forms the output surface of the light beam of the optical element. The front end part 48 of the optical element 80 is able to engage with the input end of the optical fibre 50.

Figure 4A:
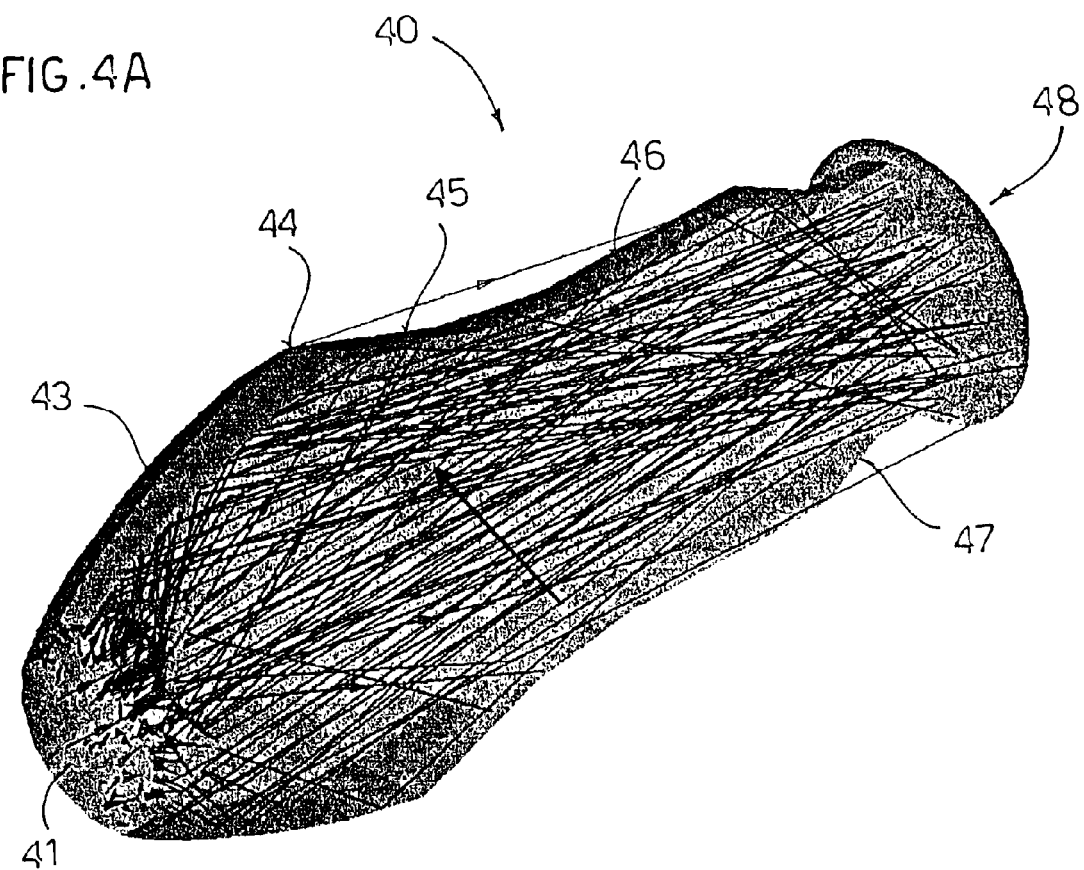
FIG. 4A is a perspective view of the optical element illustrating the propagation of light beams therein.
Figure 4B:
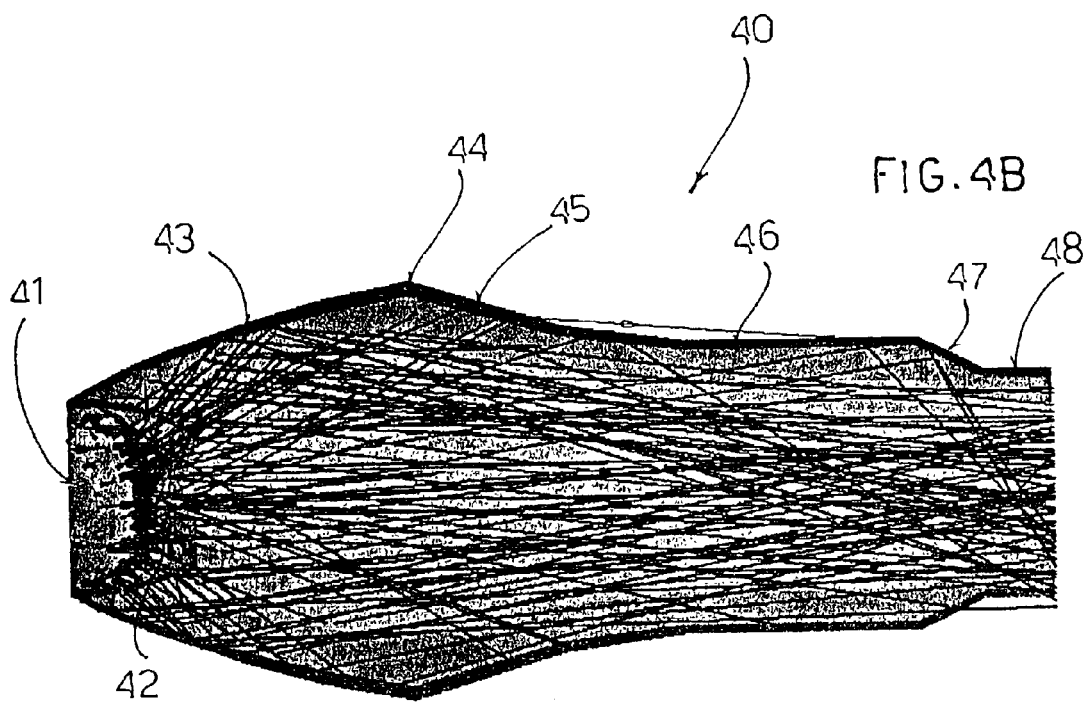
FIG. 4B is an axial sectional view of the optical element illustrating the propagation of light beams therein.

The LED 30 emits as its output a light beam contained within a cone with a half opening of about 50°. As shown in FIGS. 4A and 4B the paraboloid-shaped front wall 42 of the seat 41 formed in the optical element 40 acts directly on the light rays emitted by the LED 30, narrowing the conical light beam emitted by the LED and directing the light rays along the axis of the optical element.

The light beams which are diffracted by the side wall of the seat 41 and diverge with respect to the axis of the optical element 40, are incident on the first tapered portion, or increasing diameter portion, 43, of the side profile of the optical element 40 and are reflected toward the axis of the optical element 40. The first portion 43 of the side wall of the optical element is shaped so as to work with total reflection, directing the most divergent light beam along the axis of the optical element 40.

The second tapered portion, or decreasing diameter portion, 45, of the side wall of the optical element 40 has been designed so as not to reflect directly the light rays reflected by the first tapered, increasing diameter portion 43. Instead, the second portion 45 reflects the light beams diffracted by the front paraboloid-shaped wall 42 of the seat 41 which diverge with respect to the axis of the optical element with a smaller angle with respect to the rays that are incident on the first portion 43 of the side wall.

Consequently, the light rays incident on the second portion 45 of side wall of the optical element are reflected with an angle of reflection that is not greater than the angle of reflection generated by the first portion 43 of side wall of the optical element.

As a result a beam of light rays that remain substantially parallel to the axis of the optical element 40 and thus at right angles to the output plane of the optical element 40 and to the input plane of the optical fibre 50 is concentrated within the third cylindrical portion 46 of the side wall of the optical element.

Figure 5A:
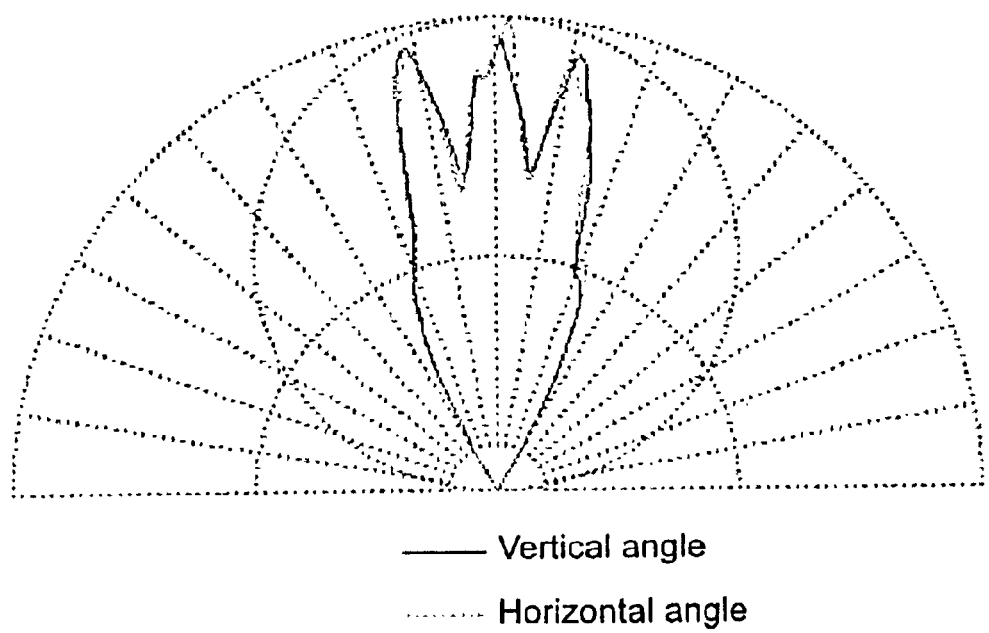
FIG. 5A is a polar diagram illustrating the distribution of the light flux leaving the optical element according to the angle of emission.
Figure 5B:
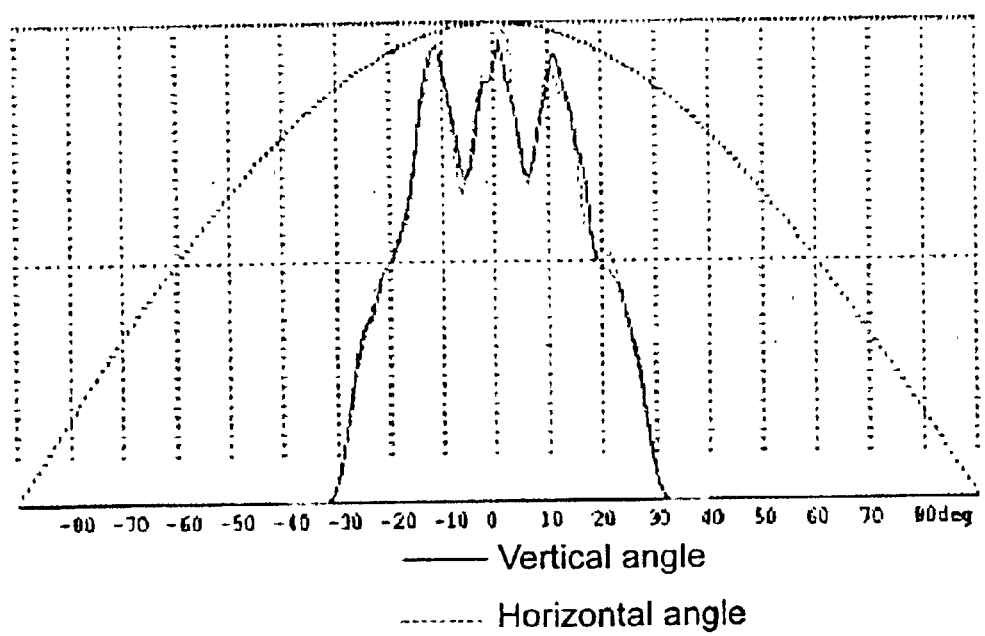
FIG. 5B is a cartesian diagram illustrating the distribution of the light flux leaving the optical element according to the angle of emission.

Using an optical element 40 of the type previously described, coupled to a light source, such as a high-flux LED, the polar and cartesian diagrams of FIGS. 5A and 5B, respectively, are obtained. The polar diagram of FIG. 5A shows, in polar coordinates, the light flux leaving the optical element 40 according to the angle with respect to the axis of the optical element. The cartesian diagram in FIG. 5B shows, in cartesian coordinates, the light flux leaving the optical element 40 according to the angle with respect to the axis of the optical element, in which the angle measured in degrees is shown on the abscissa and the quantity of light flux is shown on the ordinate.

As can be seen from the diagrams of FIGS. 5A and 5B, leaving the optical element 40 there is a light beam contained in a cone with a half-angle of about 30° with respect to the axis coinciding with the axis of the optical element 40. To be precise, three light emission peaks are detected: a central peak at 0° and two lateral peaks at ±11° with respect to the axis of the optical element.

Figure 6A:
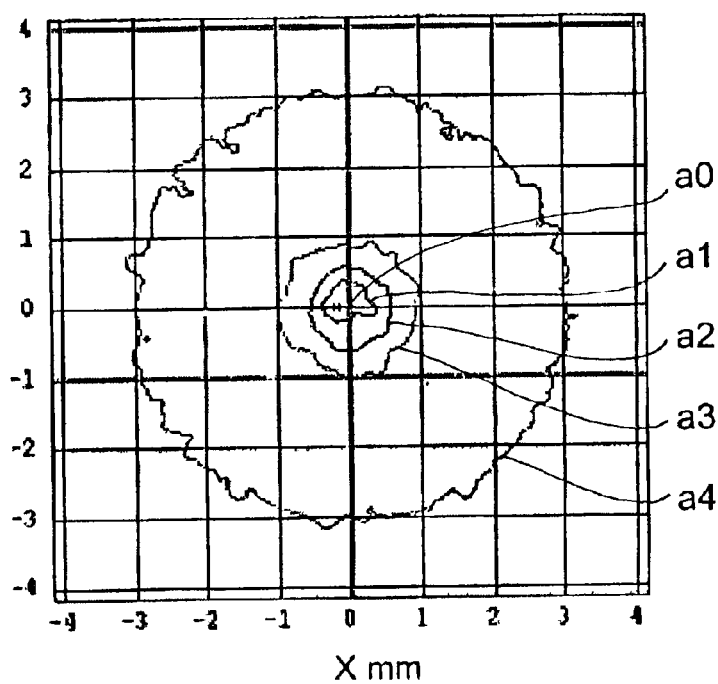
FIG. 6A is a Cartesian diagram illustrating the luminous intensity distribution per unit of surface area on the receiving or input surface of the optical fibre of the optical system according to the invention.

FIG. 6A shows a diagram in Cartesian coordinates illustrating the light emission power distribution per unit of surface area, measured in $mW/cm^2$ on the input surface of the optical fibre 50, that is to say on a plane at right angles to the axis of the optical element 40, when a LED with a light emission power of 120 mW is used. On the Cartesian plane (X, Y) coinciding with the receiving or input plane of the optical fibre, four curves $a_1$, $a_2$, $a_3$ and $a_4$ are shown, whose luminous emission power values are set forth in the table alongside. In the central point $a_0$ within the first curve $a_1$ there is a maximum luminous emission value of 1028.999 $mW/cm^2$.

Figure 6B:
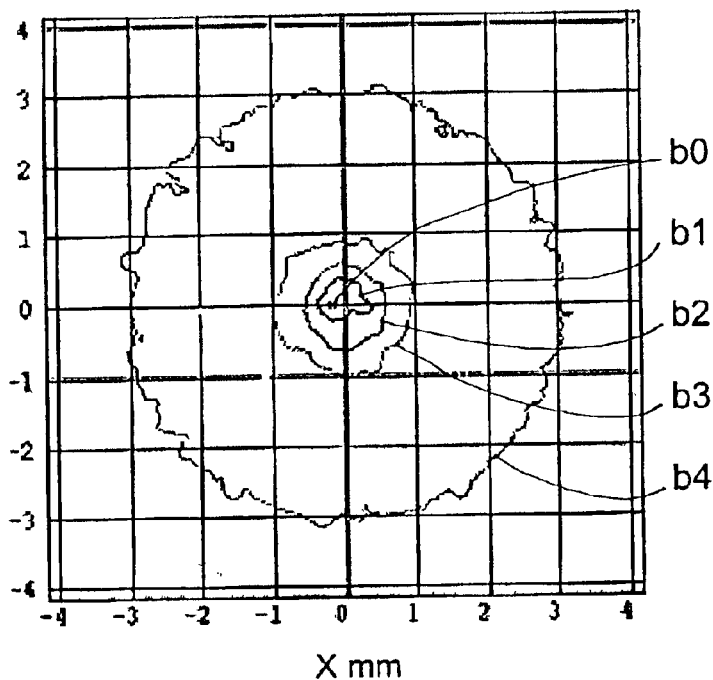
FIG. 6B is a Cartesian diagram illustrating the light intensity distribution per unit of surface area on the transmission or output surface of the optical fibre of the optical system according to the invention.

FIG. 6B is a diagram, like that in FIG. 6A, showing the luminous emission power distribution on the output surface of the optical fibre 50, in the hypothesis of the optical fibre 50 having a luminous transmission efficiency of 80%. In FIG. 6B four curves $b_1$, $b_2$, $b_3$ and $b_4$ whose light emission power is shown are shown on the Cartesian diagram alongside. The maximum light emission value of 823.1989 $mW/cm^2$ occurs at the central point $b_0$ within the first curve $b_1$.

Figure 7:
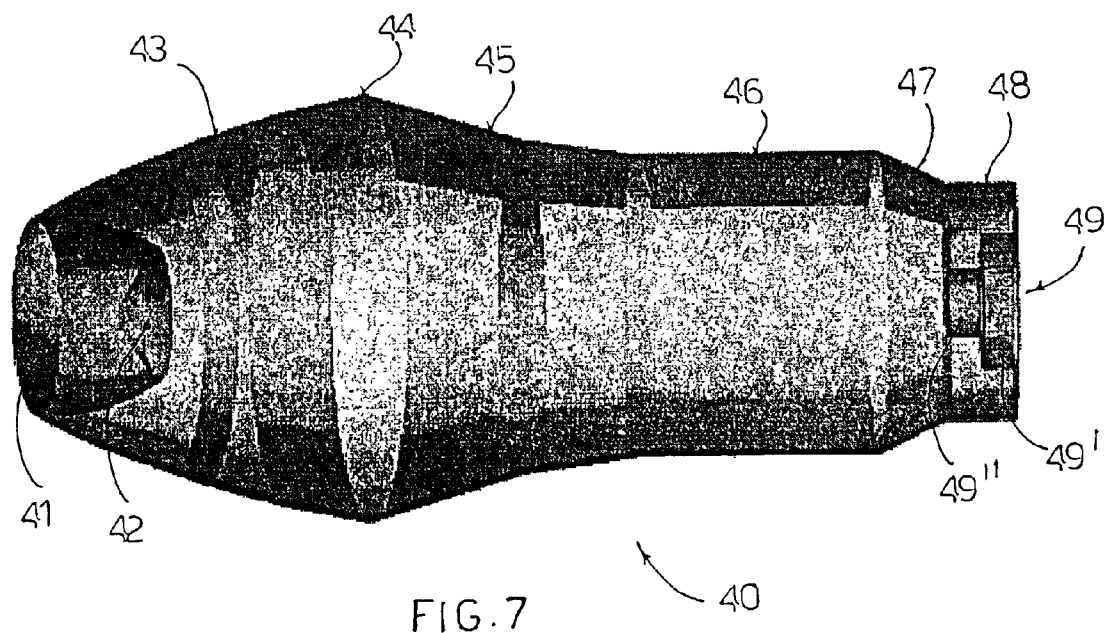
FIG. 7 is a perspective view illustrating a variant of the optical element of the optical system according to the invention.

As is apparent from said figure, in a circular area of the output surface of the optical fibre 50, having a radius of about 2 mm, there is an irregular luminous emission power distribution with some peaks concentrated above all in the central region. To overcome this drawback, as shown in FIG. 7, a variation has been made to the optical element 40. That is to say, an opening 49 disposed in an axial position has been made in the front end part 48 of the optical element 40. The opening 49 comprises a first cylindrical hole 49' with a greater diameter disposed on the output plane of the optical element 40 and a second cylindrical hole 49" with a smaller diameter disposed behind the first cylindrical hole 49', coaxial thereto and communicating therewith.

The two cylindrical holes 49' and 49" allow the light beam incident upon the input surface of the optical fibre 50 to be made more uniform and the concentration of light energy in the central part of the of the input surface of the optical fibre 50 to be reduced.

Figure 8:
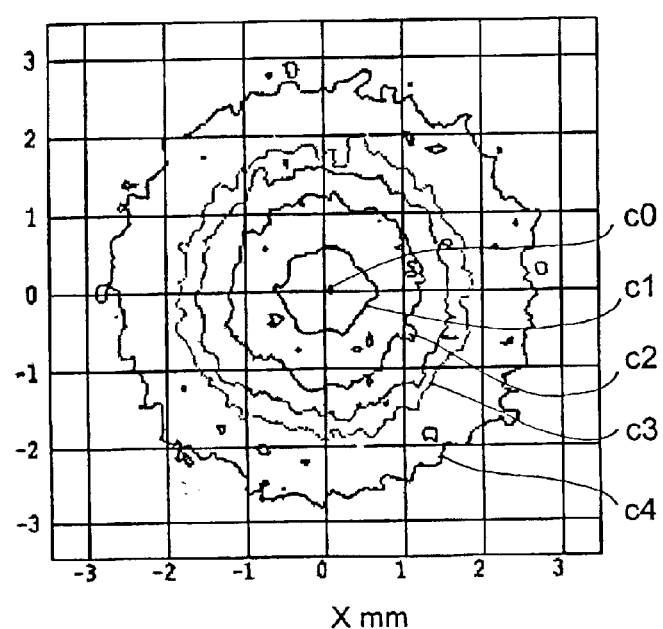
FIG. 8 is a diagram, like that of FIG. 6B, illustrating the luminous intensity distribution per unit of surface area on the output surface of the optical fibre, in the case of use of an optical element according to the variant in FIG. 7.

FIG. 8 is a diagram like that in FIG. 6B, illustrating the light emission power distribution on the output surface of the optical fibre 50, in the hypothesis that the optical fibre 50 has a light transmission efficiency of 80% and in the case of an optical element with a cylindrical opening 49 in the output wall, according to the variant in FIG. 7, being used. In FIG. 8 four curves $c_1$, $c_2$, $c_3$ and $c_4$ are shown on a Cartesian diagram and their light emission power values are shown in the table alongside. The maximum light emission value of 775.9528 $mW/cm^2$ occurs at the central point $c_0$ within the first curve $c_1$ and is less than the maximum value $b_0$ detected in the case of an optical element without the cylindrical opening at the exit. This means that a more uniform distribution of the light flux leaving the optical element 40 has been achieved.

In any case, according to this variant, in the 2-mm radius circular region on the output plane of the optical fibre 50 there is a luminous power per unit of surface area equal to 420 $mW/cm^2$ which is optimal for polymerization of resins and photosetting compounds.

Numerous variations and modifications of detail known to a person skilled in the art can be made to the present embodiment of the invention, without departing from the scope of the invention expressed by the appended claims.

We claim:

1. An optical system for a dental handpiece for the polymerization of photosetting compounds or resins comprising:

a light source mounted inside the body of the handpiece, and an optical fiber mounted at the top of the handpiece and coupled to the light source to convey and emit as its output the light emitted by the light source so as to direct it onto the area in which the photosetting compound or resin must be polymerized, wherein:

said light source comprises a single high-flux LED, and said optical system comprises an optical element able to connect said LED with said optical fibre to convey the light beam emitted by the LED toward the input end of the optical fibre, said optical element being of a shape to minimize dispersion of the light beam emitted by the LED and wherein said optical element has a substantially cylindrical shape with an axis of symmetry and has at its input end a recessed seat disposed in an axial position to receive said high-flux LED said recessed seat having an end wall having a substantially paraboloid shape, with its convexity facing toward said LED and with its axis coinciding with the axis of the optical element.

* * * * *